United States Patent [19]
Hallibert et al.

[11] Patent Number: 6,002,786
[45] Date of Patent: Dec. 14, 1999

[54] DEVICE FOR IMAGING PRINTS

[75] Inventors: Pascal Hallibert, Paris; Francis Lehomme, L'Isle-Adam; Bernard Schmitt, Cergy, all of France

[73] Assignee: SAGEM SA, Paris, France

[21] Appl. No.: 09/034,192

[22] Filed: Mar. 3, 1998

[30] Foreign Application Priority Data

Jan. 22, 1998 [FR] France .................................. 98 00658

[51] Int. Cl.⁶ ........................................................ G06K 9/00
[52] U.S. Cl. ........................................... 382/124; 382/116
[58] Field of Search ......................... 340/825.31, 825.34;
382/124, 125, 116, 126, 115, 121; 356/71;
252/501.1; 428/690, 917; 313/506, 509;
257/414, 415, 80, 81

[56] References Cited

U.S. PATENT DOCUMENTS

| | | |
|---|---|---|
| 4,336,998 | 6/1982 | Ruell . |
| 4,340,300 | 7/1982 | Ruell . |
| 5,057,244 | 10/1991 | Yukio et al. .............................. 252/501 |
| 5,448,649 | 9/1995 | Chen . |
| 5,757,278 | 5/1998 | Itsumi ................................ 340/825.31 |

OTHER PUBLICATIONS

Database WPI Section Ch, Week 8320 Derwent Publications Ltd., London, GB; AN 83–48904K XP002080114 & SU 942 684 B (As Azerb Physics), 15 juillet 1982 * abrégé *.

Database WPI Section Ch, Week 8141 Derwent Publications Ltd., London, GB; AN 81–75251D XP002080115 & SU 797 657 B (As Azerb Physics), 28 janvier 1981 * abrégé *.

Primary Examiner—Joseph Mancuso
Assistant Examiner—Vikkram Bali
Attorney, Agent, or Firm—Larson & Taylor

[57] ABSTRACT

The device for imaging finger prints has a transparent electrically insulating substrate, a thin transparent electrode on the substrate and a sensitive layer on the electrode comprising electroluminescent dielectric material, arranged to receive hand tissues whose print is to be imaged. A source means connected to said electrode applies a voltage between the electrode and tissues. A camera provides a picture taken through the substrate.

14 Claims, 1 Drawing Sheet

DEVICE FOR IMAGING PRINTS

BACKGROUND OF THE INVENTION

The present invention relates to a device for imaging prints and suitable in particular for providing a representation of a fingerprint, a palm print or a ridge pattern of human tissues for instance for identification purposes.

Numerous devices already exist that are capable of forming a recordable image of the pattern of ridges on the end phalange of a finger. However, they enable the image to be recorded by a sensor only by using an external light source (U.S. Pat. Nos. 5,448,649, 4,340,300, 4,336,998). U.S. Pat. No. 4,336,998 describes a device comprising a transparent electrically insulating substrate, a thin transparent electrode, and a sensing layer for receiving finger pressure. The sensing layer is made of a thermoplastic material, such as polystyrene. When a finger is pressed on the sensing layer, its ridges are printed therein and remain temporarily after the finger has been removed. Thereafter, the relief of the imprint is reinforced by the action of an electric field for depositing electric charges and by heating the material to soften it prior to taking the image by means of an external light source and an optical sensor.

That device has numerous shortcomings. It is not very accurate since details do not show up because the material of the sensing layer is insufficiently flexible. It takes a long time to take a print. An electrical source delivering a high voltage is required. Finally, the device cannot distinguish between a human finger and a molding of a finger.

SUMMARY OF THE INVENTION

An object of the invention to provide an improved device; it is a more specific object to provide a device which does not require an external light source and may be rendered responsive only to the application of organic tissue or of a material having equivalent electrical characteristics.

To this end, the invention provides in particular a device in which the sensitive layer is constituted by an electroluminescent dielectric material or a dielectric material in which particles of electroluminescent material, constituting as many luminophores, are dispersed. Means are provided to establish a potential difference between the tissue that is to be pressed against the sensitive layer and the thin transparent electrode.

The invention also provides a method of taking a print comprising creating virtual "elementary" capacitors by pressing the organ whose print is to be taken on an electroluminescent dielectric layer carried by a continuous electrode, applying an electric voltage between the organ and the electrode apt to energize the electroluminescent particles of the layer that are in register with the projections or ridges of the organ whose print is to be taken, and analyzing the image formed in the layer.

The luminophores may be constituted by powders similar to those used for coating flat electroluminescent screens or for making light-emitting diodes that emit in the infrared, the visible, or even the ultraviolet range; then they are dispersed in the form of microcrystals in the dielectric material. In particular, it is possible to use copper-doped zinc sulfide. It is desirable to use a dielectric material having a high dielectric constant, at least 10, and having a high light transmission coefficient at the wavelength emitted by the luminophores. Epoxy resins which present acceptable transmission when in thin layer can be used providing their dielectric coefficient is greater than 10. The higher the dielectric constant, the lower the voltage at which the luminophore begins to emit threshold voltage for a layer of given thickness. It is then possible to reduce the thickness of the sensitive layer since there is less danger of breakdown, with the advantage of increasing light transmission. It is also possible to use electroluminescent substances deposited in a thin film. It is also possible to use certain conjugate conductive polymers having intrinsic electroluminescence.

The transparent electrode will often be constituted by a thin film of indium-tin oxide, known as ITO, in widespread use in the manufacture of flat screens and LCD, which technology is thoroughly mastered and provides satisfactory adhesion for resins and varnishes.

The sensor capable of providing a signal representative of the optical image created by the sensitive layer can be of any of numerous types. It is possible to use a camera having a matrix of photosensitive sites and an optical system for forming an image of the back face of the substrate on the matrix (e.g. CCD or CMOS camera); it is also possible to use other recording media such as a photographic film. Often the matrix of photosensitive sites, selected to be sensitive to the radiation from the luminophores, can be applied directly to the rear face or can be separated therefrom by a light amplifier. A color filter can be placed between the rear face and the sensor to reduce the sensitivity of the device to ambient light.

The invention will be better understood on reading the following description of devices constituting particular embodiments given as non-limiting examples. The description refers to the accompanying drawing.

DETAILED DESCRIPTION

Figure 1:
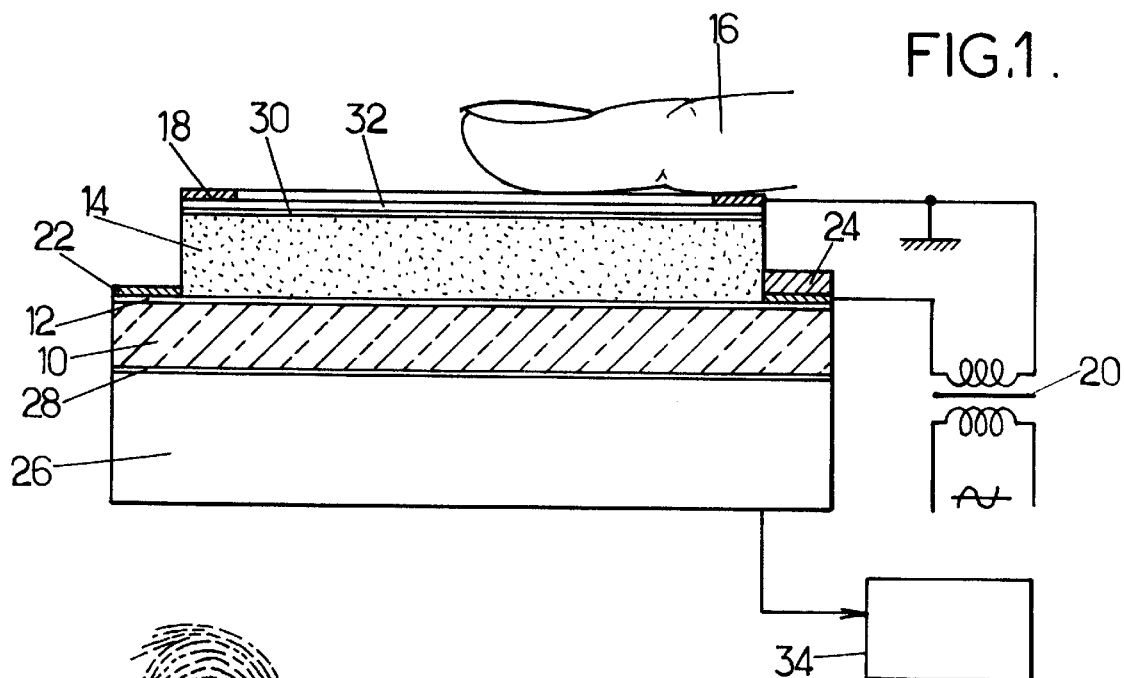
FIG. 1 is a diagram of the device, in section.

The device shown diagrammatically in FIG. 1, which is not to scale for reasons of clarity, comprises a transparent electrically insulating substrate 10 covered by a thin transparent electrode 12 which in turn supports a sensitive layer 14 for receiving pressure from an organ whose print is to be taken (e.g. a finger 16 or an entire hand).

The substrate 10 may be constituted by various substances that are transparent in the wavelength range used. In the visible range, glass will generally be used. The thin transparent electrode may be identical in structure to backing electrodes used for liquid crystal displays. In which case it is constituted by indium and tin oxide and it is a few hundreds of nanometers thick.

The sensitive layer 14 may have various structures.

In a first embodiment, it is constituted by a dielectric material in which particles of electroluminescent material are dispersed to constitute luminophores. As a general rule, the layer used will be less than 50 μm thick and will be made of a dielectric material having a dielectric coefficient greater than 20, which makes it possible to adopt a low threshold voltage below 40 volts which is effective and compatible with present safety standards. The material must also adhere in satisfactory to the thin electrode 12. Among resins and varnishes that can be used, the following resins can be mentioned specially: cyanoethyl cellulose; cyanoethyl ether of polyvinyl alcohol; acrylopolyurethane resins; and melamino formaldehyde resins.

The particles, having a grain size generally smaller than 30 μm, are at a concentration by weight in the sensitive layer lying in the range 15% to 35%, and frequently about 30% by weight. By way of example, crystals of the following materials can be used:

(ZnS):Cu
(ZnS):Mn
(ZnS):Al
(ZnS):Cu and Mn
(ZnS):Cu and Al
(ZnSe):Cu or Al or Mn
(ZnSe):CdSe
(ZnSe):ZnTe The dopant (e.g. Cu) and its concentration in the ZnS crystal structure determine the wavelength of the radiation. In more complex structures such as ZnSe: ZnTe, the emission wavelength and the light intensity can be adjusted by the proportions of each of the ingredients and the way in which they are crystallized, which is determined by the manufacturing method. Such crystals, suitable for excitation either by a DC voltage or by an AC voltage, are available on the market.

With a sensitive layer of this constitution, the method of taking a print requires a voltage applied between the finger 16 and the electrode 12. A convenient, but not exclusive, way of doing this consists in depositing a ring of conductive material 18 on a peripheral portion of the sensitive layer 14. When a finger is pressed on the sensitive layer, it also presses on the ring 13 which may be constituted by a coating.

The ridges of the finger 16 can be considered as being a virtual array of elementary capacitors associated with the electrode 12 and the sensitive layer 14.

When the luminophores are of a type that respond to a current flow, the set of "elementary capacitors" is fed by a voltage other than DC. As shown in FIG. 1, the voltage source is constituted by a transformer 20 whose primary is connected to a power supply. A "cold" terminal of the secondary is connected to the ring 18 and is grounded. The other end (hot end) of the secondary is connected to a conductive frame 22 in communication with the electrode 12. The frame may be constituted merely by a metal coating, and it may be covered by a strip 24 that is also of metal in the zone where the connection is made with the secondary winding of the transformer 20.

The voltage applied between the electrode 12 and the finger 16 depends on the nature of the current and on its frequency. For a sine-shaped alternating current, it is possible to adopt a peak-to-peak voltage of 20 V to less than 100 V. A frequency in the range 1 kHz to 50 kHz gives good results. Regarding safety, the acceptable voltage is at a higher frequency.

It is also possible to feed current in the form of unipolar pulses, or of sine-shaped, unipolar, or rectangular pulse trains.

Instead of indium-tin oxide $In_2O_3/SnO_2$, it is possible to consider using indium oxide that is pure or that contains zinc.

Figure 2:
FIG. 2 shows how a print image may appear.

Such a device provides a high definition image generated by radiation from the luminophores situated between the electrode and the points where ridges on the finger are pressed against the sensitive layer. When viewed through the substrate 10, the general appearance of the image is of the kind shown in FIG. 2. This image is sensed by a sensor 26 which may be a TV camera connected to a computer and enabling the image of the finger print to be displayed on the computer screen. Instead of using a camera, it is possible to use a solid state sensor applied directly against the bottom face of the substrate 10. A color filter 28 having a transmission peak corresponding to the wavelength of the electroluminescent material is advantageously interposed between the sensitive layer and the sensor. However that is not essential.

To increase the light efficiency of the device and to limit the contribution from ambient light, the sensitive layer 14 is advantageously covered in a film 30 of light reflecting or diffusing dielectric material and/or in an opaque film 32. The reflecting film can be constituted, in particular, by barium titanate having a thickness of about 5 $\mu$m. The opaque film 32 may be constituted, in particular, by black manganese oxide having a thickness of 5 $\mu$m to 20 $\mu$m.

Instead of using two distinct protective films, one diffusing and the other opaque, it is possible to make a single layer whose composition is varied as the layer is grown.

A device according to the invention may be made is as follows.

A transparent electrode 12 is deposited up to a thickness of about 300 nm on a glass substrate that is a few millimeters thick. Deposition can be performed, in particular, by spraying and physical vapor deposition (PVD) or chemical vapor deposition (CVD).

The thickness of the substrate 10 is selected as a function of its area. For a device that is to take fingerprints, a thickness of 5 mm is generally satisfactory.

Other layers are deposited on the electrode 12:
the sensitive layer, which is often a few tens of microns thick;
where appropriate, a reflecting film of $TiBaO_3$;
also optionally, an opaque protective layer of manganese oxide; and
the ring 18 for making contact with a finger.

The sensitive layer may be formed by spraying a mixture under pressure using a nozzle that forms a fine mist. It is also possible to use silkscreen printing or a "spin" technique for obtaining a thickness of about 10 $\mu$m.

In practice, the luminophore content of the sensitive layer is typically about 30% by weight. The thickness of the layer must be greater than the size of the crystals, which are generally smaller than 30 $\mu$m. A sensitive layer having a thickness of 30 $\mu$m to 50 $\mu$m has generally given good results.

To take a print of a finger, the finger is pressed flat on the sensitive layer or the protective film, as shown in FIG. 1, and an alternating voltage is applied. The sensor is used in conventional manner to provide a representation of the image to a computer processor system 34 which may likewise be conventional.

The device makes it possible to distinguish the finger of a living person from a molding, thereby countering fraud consisting in pressing such a molding on the device in a system for giving access to protected premises. A molding has electrical characteristics that are not the same as those of a human finger.

It should also be observed that the device also makes it possible to verify that a living finger has been applied. The pulse gives rise to cyclic variation in the image, with the bright pattern or points of the kind shown in FIG. 2 changing in intensity at the pulse rate. The computer system 34 can be designed to verify the existence of such variation.

Figure 3:
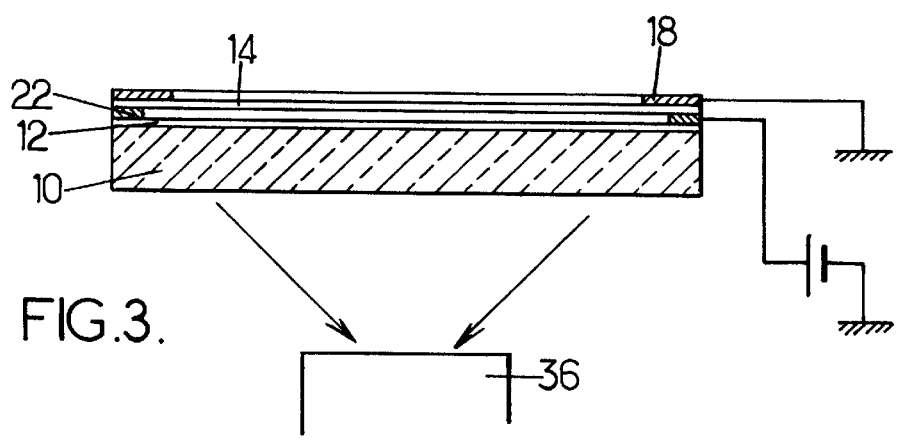
FIGS. 3 and 4 show modified embodiments.

In another embodiment, the device may be designed to be energized by a DC voltage. As shown in FIG. 3 (where members corresponding to those of FIG. 1 are given the same reference numerals), the substrate 10 again carries a thin transparent electrode 12 that is a few hundreds of nanometers thick. This electrode, generally made of ITO, can be constituted by spraying and physical vapor deposition (PVD), or by chemical vapor deposition (CVD), i.e. using one of the methods commonly used in thin film technology.

The layer 14 is generally thinner than in the case of FIG. 1 and has a high content of electroluminescent material (typically 80% to 90% by weight). In particular, it is possible to use a layer 14 made of crystals of a material such as zinc sulfide doped with copper and manganese and using a varnish having a high dielectric coefficient as a binder. A thickness of 35 $\mu$m can be achieved with conventional techniques for printing thin films: screen printing, stenciling, or spinning. The binder may be constituted, for instance, by a varnish based on melamino-formaldehyde resin based varnish.

The films carried by the sensitive layer 15 may have the same constitution as in FIG. 1. Given the small thickness of the sensitive layer, a DC voltage of about 10 V generally gives satisfactory results. When this voltage is applied, the luminophores lying in volumes defined by the ridges of a finger pressed on the device generate light under the action of the electric field caused by the voltage applied between the ridges and the electrode 12. The light diffused by the sensitive layer 14 can be picked up through the substrate 10 by a sensor such as a camera 36 connected to a computer for displaying the print and making use of the print by image processing software.

Figure 4:
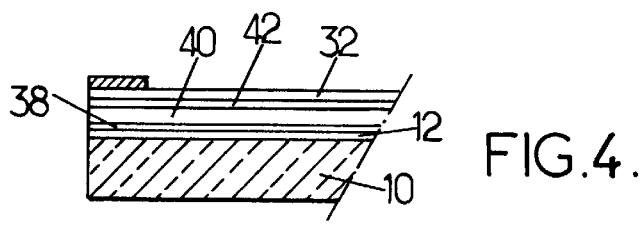

In yet another embodiment, the sensitive layer is composite and made up of a thin central zone of luminophore material, e.g. copper-doped zinc sulfide, covered on both faces by a fine dielectric film, e.g. made of: $Ta_2O_5$, $Al_2O_3$, $Al_2O_3$—$Y_2O_3$, $Al_2O_3$—$Ta_2O_5$—$Y_2O_3$, $Y_2O_3$, $ZrO_2$, $TiO_2$, $PbTiO_3$, $PbTiO_3$, $BaTiO_3$. In FIG. 4, which again is not to scale for reasons of clarity, the glass substrate 10 still carries an electrode 12, e.g. of ITO, having a thickness that may be about 300 nm. The electrode 12 carries the composite sensitive layer made up of a first dielectric film 38, e.g. of $Ta_2O_5$ that is a few hundreds of nanometers thick, a thin electroluminescent layer 40 that is, for example, approximately twice as thick as the film 38, and a second dielectric film 42 having the same constitution as the layer 38. A protective layer 32, e.g. of manganese oxide, may be deposited on the sensitive layer. The films constituting the sensitive layer may again be made by spraying and physical vapor deposition or by chemical vapor deposition. Such a constitution is particularly suitable for an AC power supply at a frequency generally lying in the range 1 kHz to 50 kHz, or a DC power supply if the luminophores used are DC responsive.

We claim:

1. A device for imaging prints of human tissues, comprising:
    a transparent electrically insulating substrate,
    a thin transparent electrode on said substrate,
    a sensitive layer on said electrode comprising electroluminescent dielectric material having a dielectric coefficient of at least 10, said layer being arranged to receive tissues whose print is to be taken, and
    means connected to said electrode for applying a voltage between said electrode and said tissues.

2. A device according to claim 1, wherein said sensitive layer consists of electroluminescent particles dispersed as micro-crystals in a dielectric binder, said particles being selected for generating IR, visible or UV light when subjected to said voltage.

3. Device according to claim 2, wherein said sensitive layer has a weight content of said particles in the range 80 to 90% and said means for applying a voltage include a DC source.

4. Device according to claim 2, wherein the means for applying a voltage are arranged to deliver an other than DC voltage having a peak to peak value of from 20 to 100 Volts at a frequency of from 1 to 50 kHz.

5. A device according to claim 1, further comprising a camera having a two-dimensional array of light sensitive sites said located to receive light from and sensitive layer through said substrate.

6. Device according to claim 5, further comprising a colour filter between said camera and said substrate.

7. Device according to claim 1, wherein said means for applying a voltage comprise a ring of electrically conducting material on a peripheral portion of the sensitive layer, connectable to an electric source and arranged for being contacted by a finger pressed on said sensitive layer.

8. Device according to claim 1, further comprising an electrically insulating film on said sensitive layer, said film being of a matter which reflects or diffuses light.

9. Device according to claim 1, further comprising an electrically insulating opaque film on said sensitive layer.

10. Device according to claim 1, wherein said sensitive layer comprises doped ZnS or SnSe in a varnish selected from the group consisting of cyanoethyl cellulose; cyanoethyl ether of polyvinyl alcohol; acrylopolyurethane resins; and melamino formaldehyde resins.

11. A device for imaging prints comprising:
    a transparent electrically insulating substrate,
    a thin transparent electrode on said substrate,
    a sensitive layer on said electrode arranged to receive tissues whose print is to be taken, and consisting of a thin central layer of electroluminescent dielectric material sandwiched between two thin dielectric films, and
    means connected to said electrode for applying a voltage between said electrode and said tissues.

12. Device according to claim 11, wherein said central layer consists of doped zinc sulfide several 100 $\mu$m thick.

13. A device for imaging finger prints comprising:
    a transparent electrically insulating substrate,
    a thin transparent electrode on said substrate,
    a sensitive layer on said electrode comprising electroluminescent dielectric material, arranged to receive fingers whose print is to be taken, and
    means connected to said electrode for applying a voltage between said electrode and said fingers, comprising a ring of electrically conducting material on a peripheral portion of the sensitive layer, connectable to an electric source and arranged for being contacted by a finger pressed on said sensitive layer.

14. A method for making a print taking device, comprising the steps of:
    depositing a thin electrically conductive coating of $In_2O_3$ or $In_2O_3$—$SnO_2$ on a transparent substrate to constitute an electrode,
    depositing a mixture of electroluminescent micro-crystals and a dielectric material on said electrode by PVD or CVD to constitute a sensitive layer having a thickness smaller than 50 $\mu$m and at least equal to a size of said microcyrstals.

* * * * *